(12) United States Patent
Shinozaki et al.

(10) Patent No.: US 11,931,325 B2
(45) Date of Patent: Mar. 19, 2024

(54) HAIR-GROWTH PROMOTING COMPOSITION AND USAGE THEREOF

(71) Applicant: Eaderm Co., Ltd., Tokyo (JP)

(72) Inventors: Shohei Shinozaki, Tokyo (JP); Kentaro Shimokado, Tokyo (JP)

(73) Assignee: EADERM CO., LTD., Tokyo (JP)

( * ) Notice: Subject to any disclaimer, the term of this patent is extended or adjusted under 35 U.S.C. 154(b) by 200 days.

(21) Appl. No.: 15/769,472

(22) PCT Filed: Oct. 18, 2016

(86) PCT No.: PCT/JP2016/080815
§ 371 (c)(1),
(2) Date: Apr. 19, 2018

(87) PCT Pub. No.: WO2017/069113
PCT Pub. Date: Apr. 27, 2017

(65) Prior Publication Data
US 2018/0303775 A1    Oct. 25, 2018

(30) Foreign Application Priority Data
Oct. 20, 2015 (JP) ................. 2015-205999

(51) Int. Cl.
| | | |
|---|---|---|
| A61K 31/155 | (2006.01) | |
| A23L 33/10 | (2016.01) | |
| A61K 8/40 | (2006.01) | |
| A61K 8/41 | (2006.01) | |
| A61K 8/43 | (2006.01) | |
| A61K 8/44 | (2006.01) | |
| A61K 8/46 | (2006.01) | |
| A61K 8/49 | (2006.01) | |
| A61K 8/60 | (2006.01) | |
| A61K 8/63 | (2006.01) | |
| A61K 8/64 | (2006.01) | |
| A61K 31/131 | (2006.01) | |
| A61K 31/145 | (2006.01) | |
| A61K 31/197 | (2006.01) | |
| A61K 31/198 | (2006.01) | |
| A61K 31/435 | (2006.01) | |
| A61K 31/437 | (2006.01) | |
| A61K 31/444 | (2006.01) | |
| A61K 31/4453 | (2006.01) | |

(Continued)

(52) U.S. Cl.
CPC ............ *A61K 31/155* (2013.01); *A23L 33/10* (2016.08); *A61K 8/40* (2013.01); *A61K 8/41* (2013.01); *A61K 8/43* (2013.01); *A61K 8/44* (2013.01); *A61K 8/46* (2013.01); *A61K 8/49* (2013.01); *A61K 8/4926* (2013.01); *A61K 8/4946* (2013.01); *A61K 8/4953* (2013.01); *A61K 8/496* (2013.01); *A61K 8/606* (2013.01); *A61K 8/63* (2013.01); *A61K 8/64* (2013.01); *A61K 31/131* (2013.01); *A61K 31/145* (2013.01); *A61K 31/197* (2013.01); *A61K 31/198* (2013.01); *A61K 31/435* (2013.01); *A61K 31/437* (2013.01); *A61K 31/444* (2013.01); *A61K 31/4453* (2013.01); *A61K 31/573* (2013.01); *A61K 31/713* (2013.01); *A61K 39/395* (2013.01); *A61K 45/06* (2013.01); *A61P 17/14* (2018.01); *A61Q 7/00* (2013.01); *C12Q 1/26* (2013.01); *G01N 33/5008* (2013.01); *C07C 257/10* (2013.01); *C07C 279/00* (2013.01); *G01N 2333/90254* (2013.01); *G01N 2500/04* (2013.01)

(58) Field of Classification Search
None
See application file for complete search history.

(56) References Cited

U.S. PATENT DOCUMENTS 5,837,738 A * 11/1998 Williamson .......... A61K 31/155
                                                          514/634
6,093,745 A *  7/2000 Hammes ............... A61K 31/155
                                                          514/634

(Continued)

FOREIGN PATENT DOCUMENTS

| AT | 413212 B | * 12/2005 | ............ C12N 5/0627 |
| CN | 101219147 A | * 7/2008 | ............ A61K 31/573 |

(Continued)

OTHER PUBLICATIONS

Nakane et al. Novel potent and selective inhibitors of inducible nitric oxide synthase. Mol. Pharmacol., 47, 831-834 (1995). (Year: 1995).*

(Continued)

*Primary Examiner* — Elizabeth C. Kemmerer
*Assistant Examiner* — Regina M DeBerry
(74) *Attorney, Agent, or Firm* — Knobbe, Martens, Olson & Bear, LLP (57) ABSTRACT

Novel compositions that promote hair growth or hair restoration, and compositions that prevent hair loss. Compositions including an iNOS inhibitor as an active ingredient are provided. Advantageous affects for hair growth or hair restoration are obtained when a composition including an iNOS inhibitor as an active ingredient is administered to a mammal. For the iNOS inhibitor, a low-molecular compound, an antibody, or a nucleic acid drug such as an antisense oligonucleotide or siRNA may be used. A method of screening for effective substances for promotion of hair growth or hair restoration or prevention of hair loss is also provided.

9 Claims, 11 Drawing Sheets (51) Int. Cl.
- *A61K 31/573* (2006.01)
- *A61K 31/713* (2006.01)
- *A61K 39/395* (2006.01)
- *A61K 45/06* (2006.01)
- *A61P 17/14* (2006.01)
- *A61Q 7/00* (2006.01)
- *C07C 257/10* (2006.01)
- *C07C 279/00* (2006.01)
- *C12Q 1/26* (2006.01)
- *G01N 33/50* (2006.01)

(56) References Cited

U.S. PATENT DOCUMENTS

| | | | |
|---|---|---|---|
| 2002/0065222 | A1 | 5/2002 | Usala |
| 2003/0083381 | A1 | 5/2003 | Kumagai et al. |
| 2016/0120803 | A1* | 5/2016 | Mathur ............ A61K 31/573 514/169 |

FOREIGN PATENT DOCUMENTS

| | | |
|---|---|---|
| JP | H07-316023 A | 12/1995 |
| JP | H10-501989 A | 2/1998 |
| JP | 2007-197330 A | 8/2007 |
| KR | 10-2013 0040664 A | 4/2013 |
| KR | 10-2013 0069019 | 6/2013 |
| KR | 10-2014 0062249 A | 5/2014 |
| KR | 10-2014 0102558 | 8/2014 |
| WO | WO 96/00006 A1 | 1/1996 |
| WO | WO 01/72268 A1 | 10/2001 |

OTHER PUBLICATIONS

Moser Medical Group Kosmetisch. Storing hair follicle micro transplants, for use in transplantation operations to restore hair growth, comprises using storage solution containing apoptosis inhibitor (aminoguanidine) to increase survival rate. Document AT413212B, English Translation p. 1-14, Dec. 2005 (Year: 2005).*

Moser Medical Group Kosmetische Haarchifurgie GMBH. Storage of Hair Follicle Micrografts. English Translation of Document AT 413212. Translated by LinguaLinx Language Solutions, Inc. pp. 1-36 (2005). (Year: 2005).*

Strub et al. The Novel Imidazopyridine 2-[2-(4-Methoxy-pyridin-2-yl)-ethyl]-3H-imidazo[4,5-b]pyridine (BYK191023) Is a Highly Selective Inhibitor of the Inducible Nitric-Oxide Synthase. Molecular Pharmacology vol. 69, No. 1, pp. 328-337, (2006). (Year: 2006).*

Garvey et al. 1400W Is a Slow, Tight Binding, and Highly Selective Inhibitor of Inducible Nitric-oxide Synthase in Vitro and in Vivo. The Journal of Biological Chemistry vol. 272, No. 8, Issue of Feb. 21, pp. 4959-4963, (1997). (Year: 1997).*

Xudong et al. Dectancyl mastication tablet for dogs and cats. English Translation of CN 101219147 Tianjin Ringtop Biotechnology Co. Ltd. (Jul. 16, 2008). (Year: 2008).*

Alderton et al. GW274150 and GW273629 are potent and highly selective inhibitors of inducible nitric oxide synthase in vivo and in vitro. British Journal of Pharmacology 145, 301-312 (2005) (Year: 2005).*

Wolf Ronald et al. "Nitric oxide in the human hair follicle: constitutive and dihydrotestosterone-induced nitric oxide synthase expression and NO production in dermal papilla cells." Journal of Molecular Medicine (Berlin Germany), vol. 81, No. 2, Feb. 2003, pp. 110-117.

Extended Search Report issued in European Patent Application No. 16857427.5, dated Aug. 8, 2019.

Boer et al., The Inhibitory Potency and Selectivity of Arginine Substrate Site Nitric-Oxide Synthase Inhibitors is Solely Determined by Their Affinity toward the Different Isoenzymes Molecular Pharmacology, 2000, vol. 58, p. 1026-1034.

Bryant et al., Suppression by Dexamethasone of Inducible Nitric Oxide Synthase Protein Expression in Vivo, A Possible Role for Lipocortin , Biochemical Pharmacology, 1998, vol. 55, p. 279-285.

Kawanaka et al., Design and Synthesis of Orally Bioavailable Inhibitors of Inducible Nitric Oxide Synthase, Identification of 2-Azabicyclo [4.1.0]heptan 3 imines, Bioorganic & Medicinal Chemistry, 2003, vol. 11, p. 1723-1743.

Muscara et al., Nitric Oxide V. Therapeutic potential of nitric oxide donors and inhibitors, American Journal Physiology, 1999, vol. 276, No. 6, 9. G1313-G1316.

Nodera et al., The role of zinc in living bodies (6), Japanese Journal of Hygiene, Apr. 2002, vol. 57, Issue 1.

Paige et al., Pharmacologic Manipulation of Nitric Oxide Signally: Target NOS Dimerization and Protein-Protein Interactions, Current Topics in Medicinal Chemistry, 2007, vol. 7, p. 97-114.

Sharma et al., Twice Weekly 5 mg Dexamethasone Oral Pulse in the Treatment of Extensive Alopecia Areata, The Journal if Dermatology, 1999, vol. 26, p. 562-565.

Stenn et al., Physiological Reviews vol. 81, No. 1, Jan. 2001, pp. 449-494.

Vallance et al., Nature Reviews Drug Discovery vol. 1,No. 12, Dec. 2002, pp. 939-950.

International Preliminary Report on Patentability in International Application No. PCT/JP2016/080815, dated Apr. 26, 2018.

Office Action dated Jun. 26, 2020 in European Patent Application No. 16857427.5.

Fischer et al., Selective iNOS Inhibition Attenuates Acetylcholine- and Bradykinin-induced Vasoconstriction in Lipopolysaccharide-exposed Rat Lungs, Anesthesiology, vol. 91, No. 6, Dec. 1999, pp. 1724-1732.

Najafi, Amir, et al. "Aminoguanidine induced apoptosis in human hepatocarcinoma HepG2 cells." *Gene Reports* 25 (2021): 101329.

Matsumura, Hiroyuki, et al. "Distinct types of stem cell divisions determine organ regeneration and aging in hair follicles." *Nature Aging* 1.2 (2021): 190-204.

Matsumura, Hiroyuki, et al. "Hair follicle aging is driven by transepidermal elimination of stem cells via COL17A1 proteolysis." *Science* 351.6273 (2016): aad4395.

Morinaga, Hironobu, et al. "Obesity accelerates hair thinning by stem cell-centric converging mechanisms." *Nature* 595.7866 (2021): 266-271.

Sasaki, Mari, et al. "iNOS inhibits hair regeneration in obese diabetic (ob/ob) mice." *Biochemical and Biophysical Research Communications* 501.4 (2018): 893-897.

* cited by examiner

FIGURE 1 ob/ob

Week iNOS-KO;ob/ob

Week

0　　2　　4
Week iNOS-KO 0　　2　　4
Week

1400W 0    2    4
Week

FIGURE 5

L-NIL

FIGURE 6

BYK191013

0 2 4
Week

HAIR-GROWTH PROMOTING COMPOSITION AND USAGE THEREOF

This application is the U.S. National Phase under 35 U.S.C. § 371 of International Application No. PCT/JP2016/080815, filed Oct. 18, 2016, designating the U.S., and published in Japanese as WO 2017/069113 on Apr. 27, 2017, which claims priority to Japanese Patent Application No. 2015-205999, filed Oct. 20, 2015, the entire contents of which are incorporated herein by reference.

FIELD OF THE ART

The present invention relates to hair growth- or hair restoration-promoting compositions, hair loss-preventing compositions, and methods of screening for hair growth- or hair restoration-promoting substances and hair loss-preventing substances. More specifically, it relates to iNOS inhibitor-comprising compositions and screening methods using the iNOS-inhibiting activity as an index.

BACKGROUND OF THE ART

Hair growth is generally classified into the growth phase (anagen), regressing phase (catagen) and resting phase (telogen) (Non-patent Document 1). In the case of human hair, after the growth phase continues for two to seven years, it goes through the regressing phase and resting phase, and then hair falls out.

The primary functions of hair are protection from trauma or direct sunlight and prevention of loss of body temperature. Hair is also important in terms of mediating social communication, and decrease of hair volume may bring about reduction of quality of life in people.

Reasons for hair loss can be classified into male pattern alopecia, seborrheic alopecia, senile alopecia, alopecia areata, drug alopecia caused by administration of an anticancer agent, scarring alopecia, postpartum alopecia occurring after childbirth, and such. However, ways of dealing with these alopecias have not been established as of now.

The major hair growing agents/hair tonics currently approved as pharmaceuticals include minoxidil and finasteride. Minoxidil is a pharmaceutical originally developed as an oral hypertensive drug that works mainly on blood vessel dilation. In patients receiving treatment of the hypertensive drug, vasodilation and hypertrichosis such as facilitation of hair root regeneration were observed; and thus, the pharmaceutical was newly developed as an external hair growth agent for medical use. Minoxidil dilates blood vessels by activating ATP-sensitive K channels. It is thought that the main functions of minoxidil are to stimulate hair growth by promoting the transfer of hair follicles from the resting phase to the initial growth phase, and make hair follicles grow to grow the hair thick. DHT (dihydrotestosterone) links to the sebaceous gland receptor, and has the effect of inhibiting hair growth. Finasteride works by inhibiting type II 5-α reductase which is an enzyme that converts male hormone testosterone to DHT, and suppressing DHT synthesis. The pharmaceutical was developed by applying the drug to treatment of prostatic hypertrophy, which is caused by male hormone, as a therapeutic agent for androgenetic alopecia (AGA).

Despite that these pharmaceuticals are currently on the market, more effective medicaments are in demand for countermeasures against hair loss.

Nitric oxide synthase (NOS, EC1.14.13.39) is an enzyme involved in the synthesis of nitric oxide (NO) which is an oxide of nitrogen. NOS is classified into constitutive NOS (cNOS) which is present at a certain quantity within normal cells, and inducible NOS (iNOS, NOS2) induced by inflammation or stress, and cNOS is further classified into neural nNOS (NOS1) and vascular endothelial eNOS (NOS3) (Non-patent Document 2). iNOS is induced by lipopolysaccharide (LPS) known as an inflammatory stimulator, and it is expressed in the immune system, cardiovascular system, lungs and such. iNOS is known to be involved in biological defense against pathogens. Until now, iNOS inhibitors have been developed for use as anti-inflammatory drugs or anti-cancer agents or for the purpose of treating sepsis or such; however, it has not reached the development of therapeutically effective pharmaceutical agents including beauty supplements and cosmetics.

PRIOR ART DOCUMENTS

Non-Patent Documents

[Non-patent Document 1] K. S. Stenn and R. Paus, PHYSIOLOGICAL REVIEWS Vol. 81, No. 1, January 2001, pp. 449-494

[Non-patent Document 2] Patrick Vallance & James Leiper, Nature Reviews Drug Discovery Vol. 1, No. 12, December 2002, pp. 939-950

SUMMARY OF THE INVENTION

Problems to be Solved by the Invention

One of the objectives of the present invention is to provide novel compositions that promote hair growth or hair restoration, and compositions that prevent hair loss. Further, another objective of the present invention is to provide a new method of screening for substances that promote hair growth or hair restoration and substances that prevent hair loss.

Means to Solve the Problem

The inventors discovered that hair growth is promoted in the iNOS-deficient ob/ob mouse which was created for the purpose of elucidating the connection between inflammation and diabetes. Further, they found that hair growth is promoted in the iNOS single-deficient mouse in comparison to the wild type. Then, they confirmed that several existing iNOS inhibitors exert effects on hair growth. The present invention is based on these findings, and relates to specifically the matters below.

[1] A composition for use in promotion of hair growth or hair restoration or prevention of hair loss, which comprises an iNOS inhibitor as an active ingredient.

[2] The composition described in [1], wherein the iNOS inhibitor is a compound selected from the group consisting of 1400W, aminoguanidine, BYK191023, AMT hydrochloride, AR-C102222, L-NIO, L-NIL, S-ethylisothiourea, S-methylisothiourea, S-aminoethylisothiourea, 2-iminopiperidine, butylamine, ONO-1714, L-NG-nitroarginine, L-NG-monomethylarginine, L-nitroarginine methyl ester, and dexamethasone.

[3] The composition described in [1], wherein the iNOS inhibitor is a monoclonal antibody or a fragment thereof.

[4] The composition described in [1], wherein the iNOS inhibitor is an antisense oligonucleotide.

[5] The composition described in [1], wherein the iNOS inhibitor is an siRNA.

[6] The composition described in [1], which is a pharmaceutical composition.

[7] The composition described in [1], which is a cosmetic composition.

[8] The composition described in [1], which is a beauty supplement.

[9] The composition described in [1], which is an oral preparation.

[10] The composition described in [1], which is an injectable preparation.

[11] The composition described in [1], which is an external preparation.

[12] A method of promoting hair growth or hair restoration or preventing hair loss in a mammal, which comprises administering an iNOS inhibitor to the mammal.

[13] The method described in [12], wherein the mammal is a human.

[14] The method described in [12], wherein the mammal is a dog, cat or sheep.

[15] A method of promoting hair growth or hair restoration or preventing hair loss in a mammal, which comprises inhibiting iNOS.

[16] Use of an iNOS inhibitor in the manufacture of a medicament for use in promotion of hair growth or hair restoration or prevention of hair loss.

[17] A method of screening for an effective substance for promoting hair growth or hair restoration or preventing hair loss, which comprises i) contacting a test substance with iNOS in vitro, ii) measuring iNOS activity, and iii) determining whether the test substance reduces the iNOS activity.

[18] A method of inhibiting hair growth, which comprises administering an iNOS activity-enhancing composition to increase the iNOS activity.

[19] A method of inhibiting hair growth, which comprises administering a NO-generating composition to a subject.

EMBODIMENTS

Hereinbelow, the present invention is explained in detail. The inventors discovered that hair growth is promoted in the iNOS deficient ob/ob mouse created for the purpose of elucidating the connection between inflammation and diabetes. Further, they found that hair growth is promoted also in the iNOS single-deficient mouse compared to the wild type. In addition, they discovered that the exisiting iNOS inhibitors exhibit an effect on hair growth.

Compositions that Promote Hair Growth or Hair Restoration

One of the embodiments of the present invention is a composition used for promotion of hair growth or hair restoration or prevention of hair loss, and relates to a composition comprising an iNOS inhibitor as an active ingredient.

iNOS

Nitric oxide synthase (NOS, EC1.14.13.39) is an enzyme involved in the synthesis of nitric oxide (NO) which is an oxide of nitrogen. NOS is classified into constitutive NOS (cNOS) which is present at a certain quantity within normal cells, and inducible NOS (iNOS, NOΩ) induced by inflammation or stress, and cNOS is further classified into neural nNOS (NOS1) and vascular endothelial eNOS (NO53).

iNOS (induced Nitrix Oxide Synthase) is one of the inducible NOS induced by inflammation or stress, and its expression is seen in the immune system, cardiovascular tissues and cells, lungs and such. iNOS is known to be involved in biological defense against pathogens. iNOS induced by stimulation of inflammatory cytokines or bacterial toxins produces a large quantity of NO, and exhibits toxicity towards surrounding cells by reacting with reactive oxygen. The iNOS-derived NO does not exhibit toxicity merely to nonautologous cells. For example, a large quantity of the NO derived from iNOS induced by bacterial toxins in vascular smooth muscles causes powerful vasodilation and excessive permeability exasperation, and induces endotoxin shock. Further, it is noted that the NO derived from iNOS induced in glial cells or such causes denaturation or deciduation of central neurons, and iNOS is also involved in cell damage seen in autoimmune diseases such as Type I diabetes.

iNOS Inhibitors

An iNOS inhibitor can inhibit the activity of iNOS or suppress its expression. Further, an iNOS inhibitor can be a selective iNOS inhibitor or a non-selective iNOS inhibitor. An iNOS inhibitor may be, for example, a low-molecular compound, an antibody, or a polymer such as a nucleic acid.

Low-Molecular iNOS Inhibitors

As a low-molecular compound that inhibits iNOS, for example, a selective iNOS inhibitor marketed by Tocris Bioscience, 1400W, can be used. 1400W inhibits binding of the coenzyme NADPH. L-NIL is another low-molecular inhibiting agent, and an analogue of the substrates, arginine and thiocitrulline. Aminoguandine is an analogue of the substrates, arginine and thiocitrulline, and works as an irreversible iNOS inhibitor. BYK190123 inhibits the formation of iNOS dimers (iNOS can produce NO by becoming dimers).

Other selective iNOS inhibitors are, for example, S-ethylisothiourea, S-methylisothiourea, S-aminoethylisothiourea, 2-iminopiperidine, butylamine, ONO-1714 (fusion piperidine derivative; (1S, 5S, 6R, 7R)-7-chloro-3-imino-5-methyl-2-azabicyclo[4.1.0] heptane hydrochloride, AMT hydrochloride (2-amino-5,6-dihydro-6-methyl-4H-1,3-thiazine salt), AR-C102222, or such. A non-selective iNOS inhibitor is, for example, L-N$^G$-nitroarginine, L-N$^G$-monomethylarginine, L-nitroarginine methyl ester, L-NIO or such. A suppressive agent of the iNOS expression is dexamethasone. These iNOS-inhibiting low-molecular compounds can be used in the form of a pharmaceutically acceptable salt or derivative.

Anti-iNOS Antibodies

An iNOS inhibitor may be an anti-iNOS antibody. For the anti-iNOS antibody, a polyclonal antibody or a monoclonal antibody can be used, and it is preferable to use a monoclonal antibody. As long as it is an antibody that has an inhibitory activity towards iNOS, it does not have to be full length and an antibody fragment can be used. The mammal from which the antibody is derived is not particularly limited, and a human antibody, mouse antibody, rat antibody, rabbit antibody, sheep antibody or such can be used. When the antibody is used on human, any of a human antibody, humanized antibody and chimeric antibody can be used, and a human antibody is preferred. Further, the antibody or a fragment of the antibody may comprise a peptide sequence identified by screening such as the phage display method. Further, aptamers composed of nucleic acids can be used the same way as regular antibodies.

An iNOS inhibitor may be an anti-iNOS antisense oligonucleotide. For the antisense oligonucleotide, for example, an oligonucleotide of 10 to 50 bases can be designed based on the nucleotide sequence of an iNOS gene. The antisense oligonucleotide can include RNA, DNA and other modified nucleic acids. The antisense oligonucleotide may be completely complementary to the target sequence, or may contain one or several mismatches. The iNOS gene nucleotide sequences are known, and can be acquired from, for example, a database such as GenBank:
NOS2 nitric oxide synthase 2, inducible [*Homo sapiens* (human)]
  Gene ID: 4843
  mRNA: NM_000625.4
Nos2 nitric oxide synthase 2, inducible [*Mus musculus* (house mouse)]
  Gene ID: 18126
  mRNA: NM_001313921.1
siRNA An iNOS inhibitor may be an siRNA targeting iNOS. The iNOS gene nucleotide sequences are known, and can be acquired from, for example, a database such as GenBank.

Pharmaceutical Compositions

One of the embodiments of the present invention relates to pharmaceutical compositions characterized in comprising an iNOS inhibitor as an active ingredient, which are pharmaceutical compositions used for promotion of hair growth or hair restoration or prevention of hair loss. In other words, one of the embodiments of the present invention relates to use of an iNOS-inhibiting agent in the manufacturing of a pharmaceutical for use in the promotion of hair growth or hair restoration or prevention of hair loss. For the iNOS inhibitor that works as an active ingredient, for example, a low-molecular compound, an antibody, an antisense oligonucleotide, an siRNA or such described above can be used. The pharmaceutical compositions of the present invention can take on any arbitrary form of a tablet, powder, liquid, semi-solid or such, and can comprise an adequate excipient or additive in addition to the iNOS inhibitor. Further, the pharmaceutical compositions of the present invention may be combined with another active ingredient such as minoxidil and finasteride. The blending quantity of each ingredient can be appropriately determined within the acceptable range as a pharmaceutical. Further, the amount of a composition to be administered can be adequately determined according to the type of inhibiting agent used and the subject to be administered. The route of administration can also be suitably determined according to the type of inhibiting agent used and the subject to be administered.

The pharmaceutical compositions of the present invention can be used for treatment or prevention of alopecia or hair thinning. For the type of alopecia, male pattern alopecia, seborrheic alopecia, senile alopecia, alopecia areata, drug alopecia caused by administration of an anti-cancer agent or such, scarring alopecia, postpartum alopecia occurring after childbirth, and mental-disorder alopecia can be listed, without being limited thereto.

Cosmetic Compositions

One of the embodiments of the present invention relates to cosmetic compositions characterized in comprising an iNOS inhibitor as an active ingredient, which are cosmetic compositions used for promotion of hair growth or hair restoration or prevention of hair loss. For the iNOS inhibitor that works as an active ingredient, for example, a low-molecular compound, an antibody, an antisense oligonucleotide, an siRNA or such described above can be used. The cosmetic compositions of the present invention can take on any arbitrary form of a liquid, emulsion, gel, cream or such. The content of the iNOS inhibitor can be appropriately determined according to the type of inhibiting agent used and the subject to be applied.

Beauty Supplements

One of the embodiments of the present invention relates to beauty supplements characterized in comprising an iNOS inhibitor as an active ingredient, which are beauty supplements used for promotion of hair growth or hair restoration or prevention of hair loss. For the iNOS inhibitor that works as an active ingredient, for example, a low-molecular compound, an antibody, an antisense oligonucleotide, an siRNA or such described above can be used. The beauty supplements of the present invention can take on any arbitrary form of a tablet, powder, liquid or such. The beauty supplements of the present invention may be prepared to be, for example, ingested orally one to three times a day, before, during or after meals.

Methods for Promoting Hair Growth or Hair Restoration and Methods for Preventing Hair Loss One of the embodiments of the present invention relates to methods for promoting hair growth or hair restoration or preventing hair loss in a mammal. Such methods can comprise inhibiting iNOS and more specifically, for example, administering an iNOS inhibitor to the mammal. The mammal includes, for example, human, monkey, mouse, rat, rabbit, sheep, goat, *lama*, horse, mink, fox, stoat, raccoon, chinchilla, sea otter, otter, beaver, and seal. The amount to be administered can be appropriately determined according to the type of inhibiting agent to be used and the subject to be administered. The route of administration can also be suitably determined according to the type of inhibiting agent to be used and the subject to be administered. A preferred route of administration is, for example, application or spraying of a liquid agent, lotion agent, or cream agent to the epilation area, and alternatively, subcutaneous injection of a liquid agent, or oral administration of a solid agent or liquid agent. A patch containing an iNOS inhibitor may be prepared and applied to the skin.

Screening Method

One of the embodiments of the present invention relates to a method of screening for substances effective for promotion of hair growth or hair restoration or prevention of hair loss. Such screening method may include the following steps of i to iii:
(i) contacting a test substance with iNOS in vitro,
(ii) measuring the activity of iNOS, and
(iii) determining whether or not the test substance reduces the iNOS activity.

Measurement of the iNOS activity can be carried out by a skilled artisan using any arbitrary method of public knowledge. Substances identified by the screening method described above are useful as ingredients of compositions of the present invention for use in the promotion of hair growth or hair restoration or prevention of hair loss. Further, in the methods of the present invention for promoting hair growth or hair restoration or preventing hair loss in a mammal, they are also useful as substances to be administered to the mammal.

Methods of Inhibiting Hair Growth

One of the embodiments of the present invention relates to a method of inhibiting hair growth, which comprises enhancing the iNOS activity. Such a method may comprise administering a composition that enhances the iNOS activity. The iNOS activity may be enhanced by, for example, inducing the expression of iNOS in cells. It is already known that the iNOS expression is, for example, induced by LPS or cytokine, and without limitations thereto, any arbitrary substance that induces the iNOS expression may be used. Further, another embodiment of the present invention includes a composition that inhibits hair growth, which comprises an iNOS-activity enhancing substance.

One of the embodiments of the present invention relates to a method of inhibiting hair growth, which comprises administering to a subject a composition that generates NO (a composition comprising a NO-donating agent or a NO donor). Such a NO-generating medical agent includes specifically SNAP, GSNO, CysNO, NOR and NOC, without being limited thereto. The method of administration can be appropriately determined based on the property and convenience of the medical agent used and includes, for example, application or spraying of a liquid agent, lotion agent, or cream agent, and alternatively, subcutaneous injection of a liquid agent, or oral administration of a solid agent or liquid agent. Further, another embodiment of the present invention includes a composition for inhibiting hair growth, which comprises a medical agent that generates NO (a NO-donating agent or a NO donor).

Hereinbelow, the present invention will be explained in detail with the Examples, and the present invention is not limited in any way thereby.

EXAMPLES

Example 1; Hair Growth Experiment Using iNOS-Deficient Mice

Figure 1:
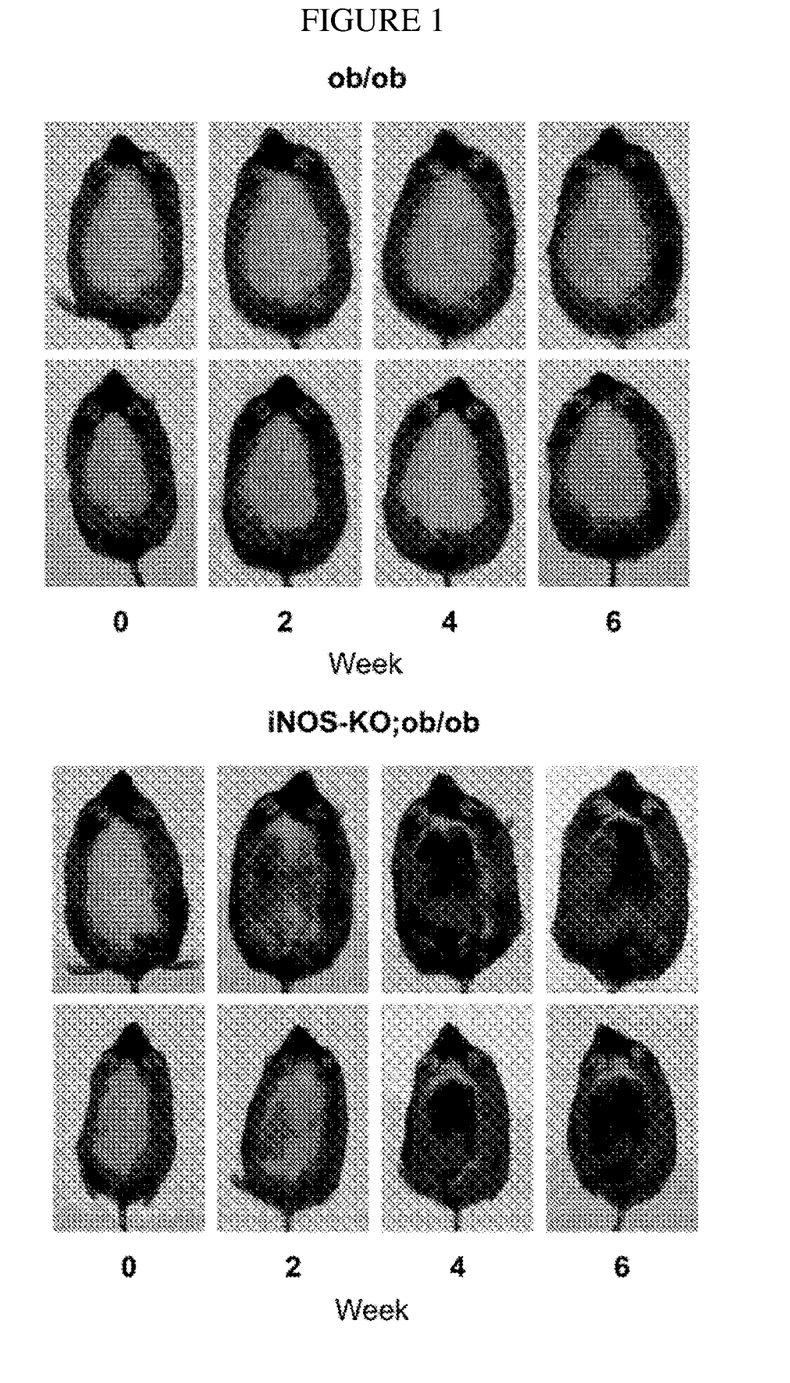
FIG. 1 A figure that shows the course (6 weeks) of hair growth in the iNOS deficient ob/ob mice and ob/ob mice (the upper row and lower row are different individuals).

The iNOS-KO mouse purchased from Jackson Lab was mated with an ob/ob mouse, and an iNOS-KO; ob/ob mouse was generated. For the control-group ob/ob mouse, the ob/ob mouse produced by crossing iNOS(+/+); ob(+/−) individuals obtained in the mating process was used. The experiment was begun using male individuals at 8 weeks of age. The whole back of the ob/ob mouse was shaved using an electric shaver under anesthesia (mixed anesthesia of ketamine hydrochloride and xylazine hydrochloride), and the hair was removed with a commercially available depilatory cream (Epilat hair removal cream from Kracie Holdings, Ltd.); and hair growth was not observed even after one month had passed. Meanwhile, deposition of melanin pigments was observed in the skin two weeks after hair removal in the iNOS-KO; ob/ob mouse, and hair growth over a wide area was confirmed three weeks later and returned to almost the original condition six weeks later (FIG. 1).

Figure 2:
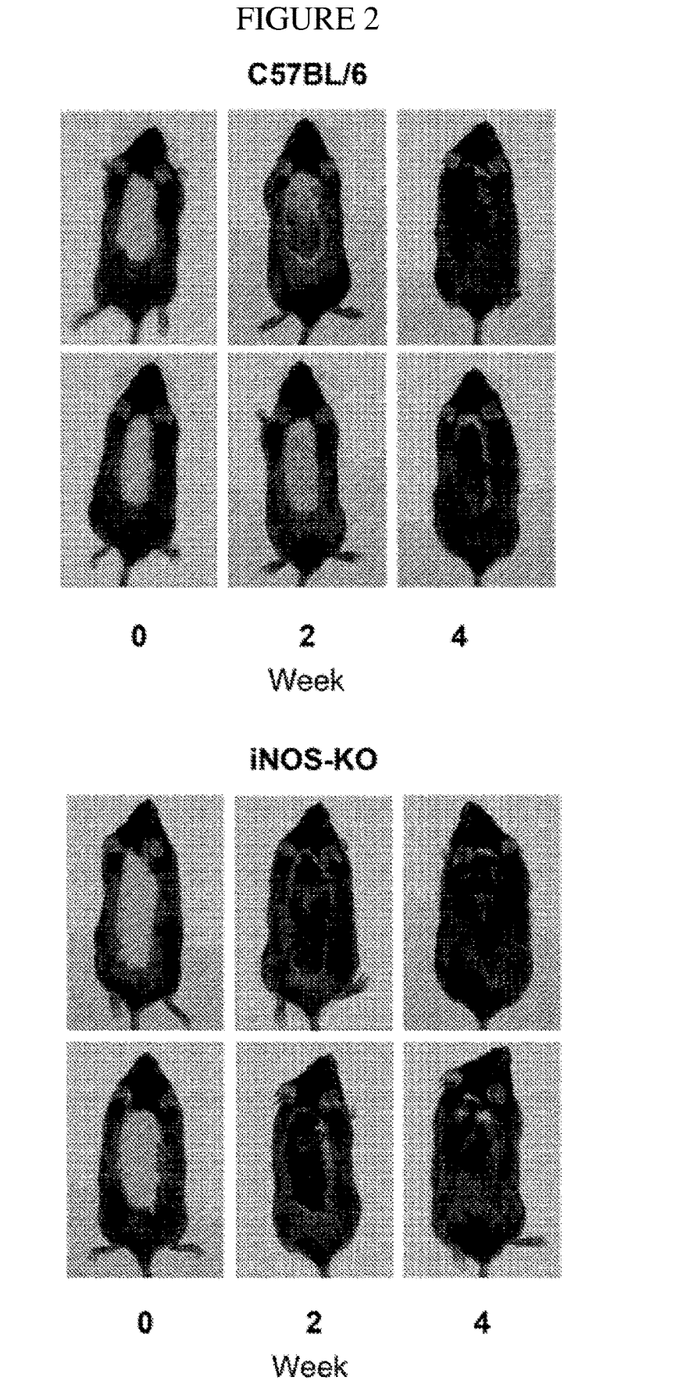
FIG. 2 A figure that shows the course (4 weeks) of hair growth in the iNOS knockout mice and wild-type mice (the upper row and lower row are different individuals).

In the normal mouse (C57BL/6 line) obtained in the mating process of the ob/ob mice, deposition of melanin pigments was observed one week after hair removal, and the hair was grown back to nearly the original state one month later. On the other hand, in the iNOS single-deficient mouse obtained in the mating process of the iNOS-KO; ob/ob mice, the hair growing process was facilitated more than that in the normal mouse, and hair growth was observed one week after hair removal and the hair grew back to almost the original state two weeks later (FIG. 2).

Results from observing these iNOS knockout mice show that hair growth may be facilitated by suppressing the iNOS activity. Further, these results are suggesting that not only gene knockout but other methods to suppress the iNOS activity, for example, use of any arbitrary low-molecular inhibiting agent, can also attain the same results. Moreover, vice versa these observations also suggest that hair growth can be suppressed by enhancing the iNOS activity.

Example 2: Hair Growth Experiment Using an iNOS Inhibitor

For this experiment, the ob/ob mouse purchased from Sankyo Labo Service Corporation was used. The whole back of the mouse was shaved using an electric shaver under anesthesia (mixed anesthesia of ketamine hydrochloride and xylazine hydrochloride) at 8 weeks of age, and the hair was removed with a commercially available depilatory cream (Epilat hair removal cream from Kracie Holdings, Ltd.). Administration or application of each iNOS inhibitor was carried out on the day the experiment began. The usage and dosage of the iNOS inhibitors used are as described below. Selective iNOS inhibitors, 1400W, L-NIL and BYK191023, were purchased from Tocris Bioscience and dissolved in saline solution, and each of them was administered intraperitoneally at 10 mg/kg, 20 mg/kg and 30 mg/kg. For the control group, saline solution was administered intraperitoneally. Consecutive administration for five days from Monday to Friday was continued for one month. A similarly selective iNOS inhibitor, aminoguanidine, was purchased from Tokyo Chemical Industry Co., Ltd. and dissolved in saline solution to 10% (w/v), and 100 μl was applied to the epilation area. For the control group, saline solution was used. Consecutive application for five days from Monday to Friday was continued for one month. The back was photographed once a week and observation was continued until 12 weeks of age. Every seven days from the start of the administration, the state of hair growth in the shaved area was rated using the hair growth score standard below.

Figure 3:
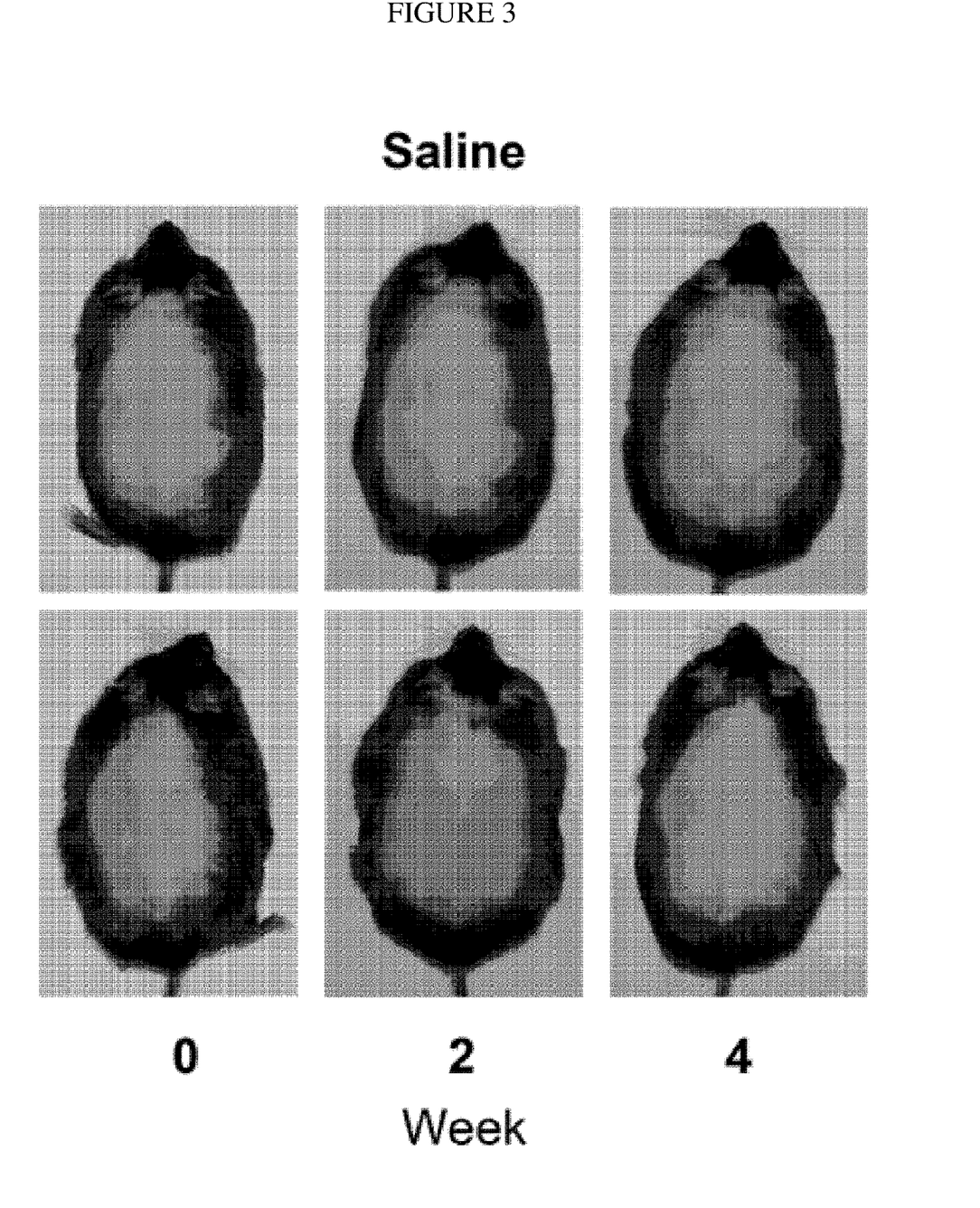
FIG. 3 A figure that shows the course (4 weeks) of hair growth in the saline solution-administered ob/ob mice (the upper row and lower row are different individuals).
Figure 4:
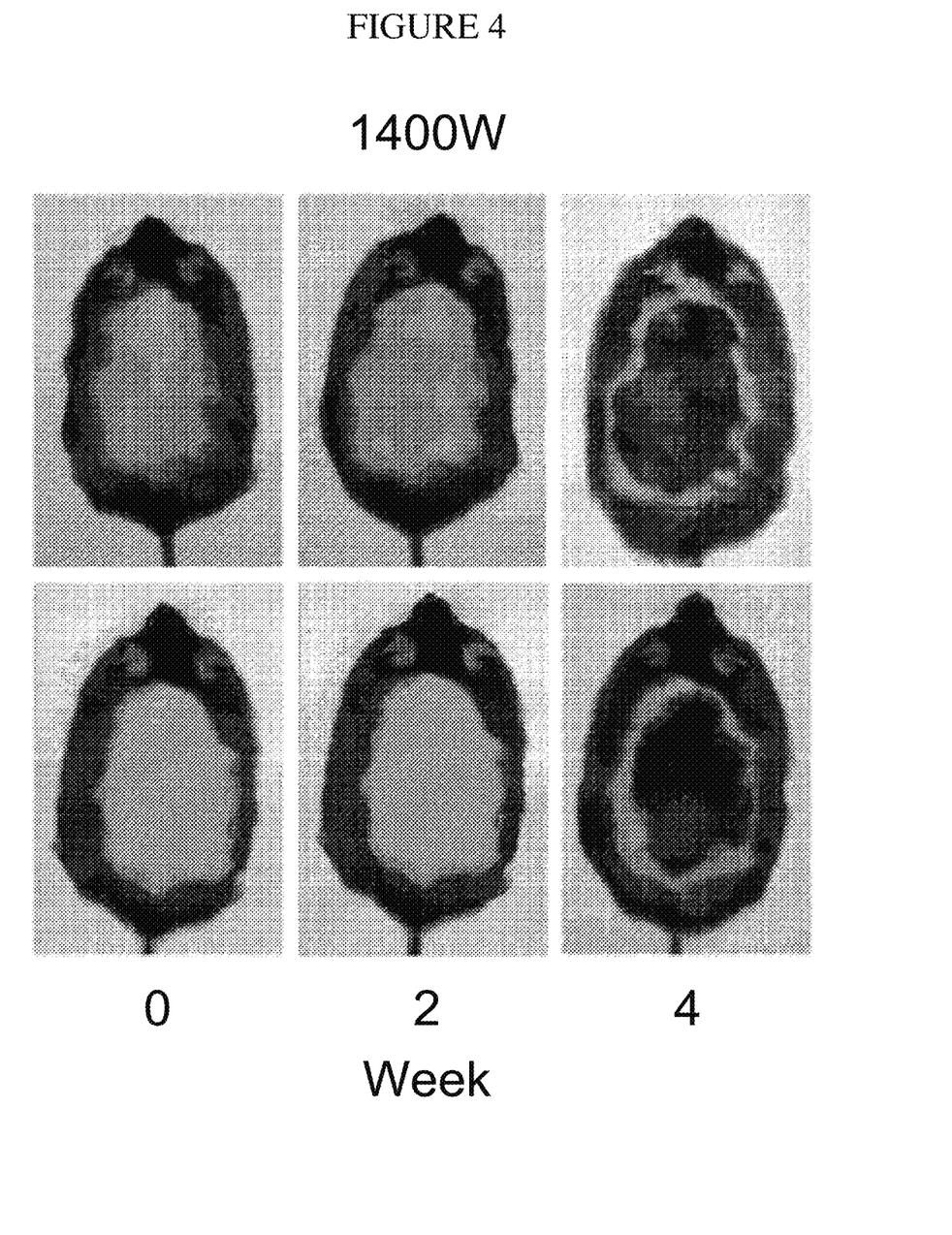
FIG. 4 A figure that shows the promotion (4 weeks) of hair growth by an iNOS inhibitor (1400W) (the upper row and lower row are different individuals).
Figure 5:
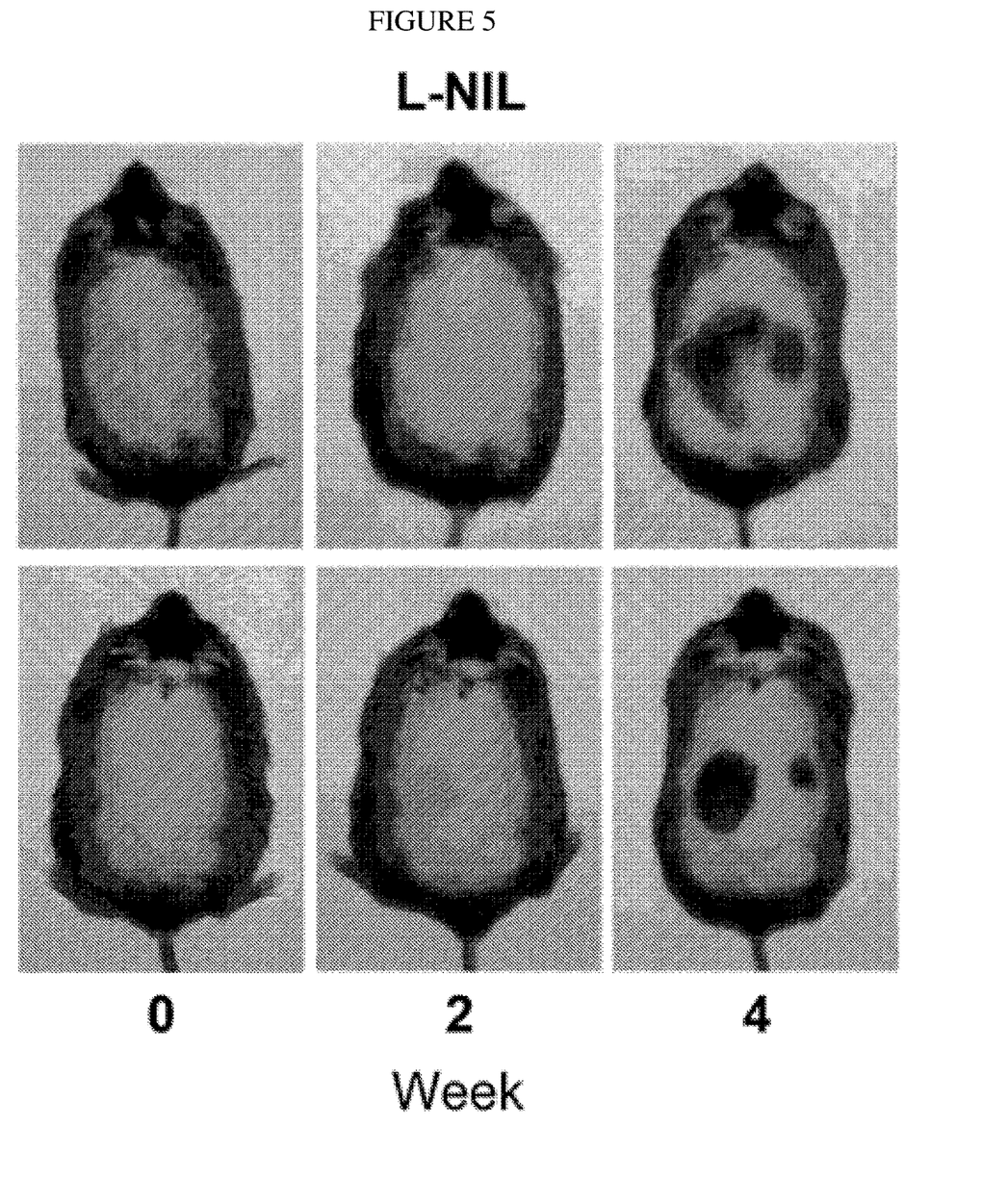
FIG. 5 A figure that shows the promotion (4 weeks) of hair growth by an iNOS inhibitor (L-NIL) (the upper row and lower row are different individuals).
Figure 6:
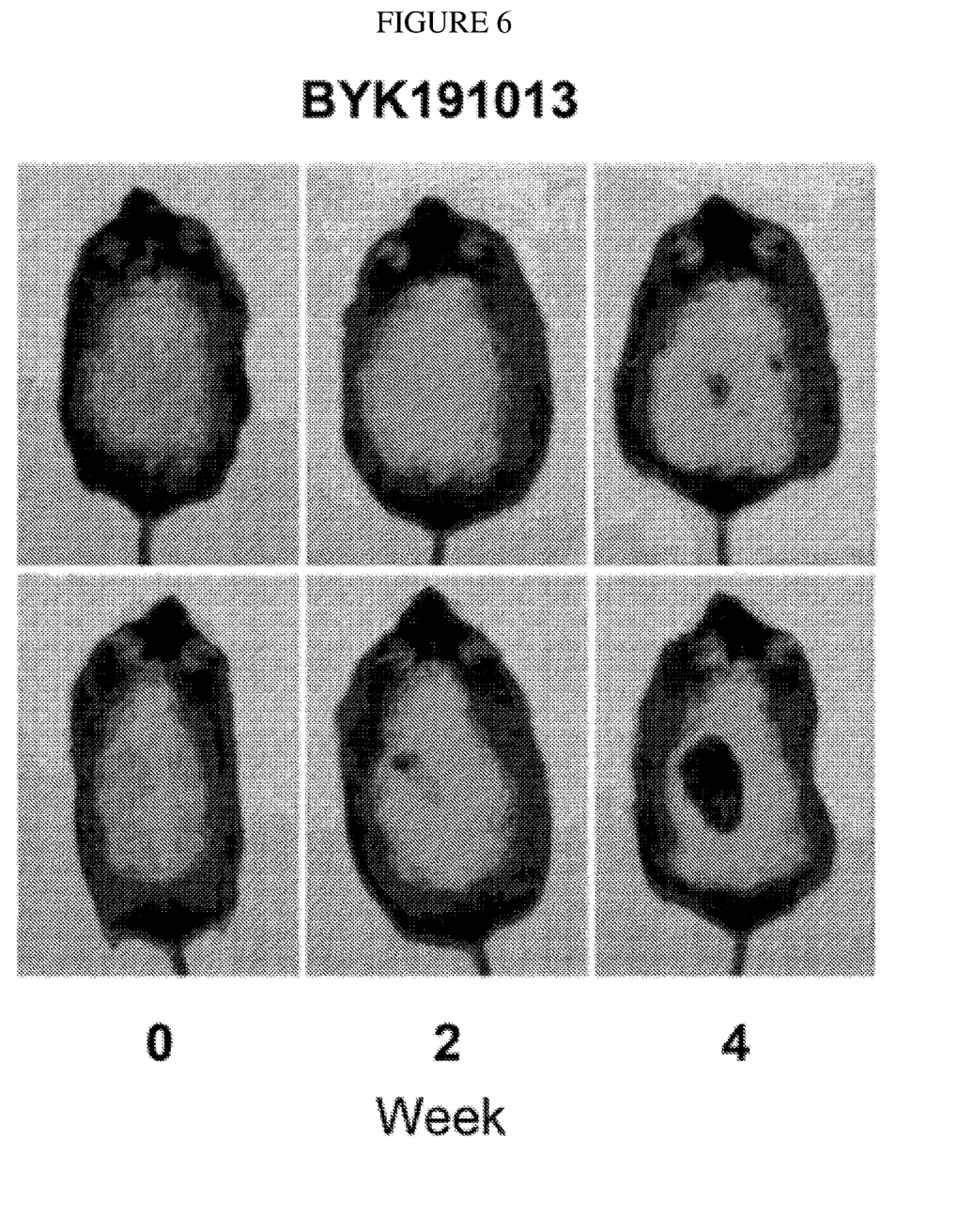
FIG. 6 A figure that shows the promotion (4 weeks) of hair growth by an iNOS inhibitor (BYK191013) (the upper row and lower row are different individuals).
Figure 7:
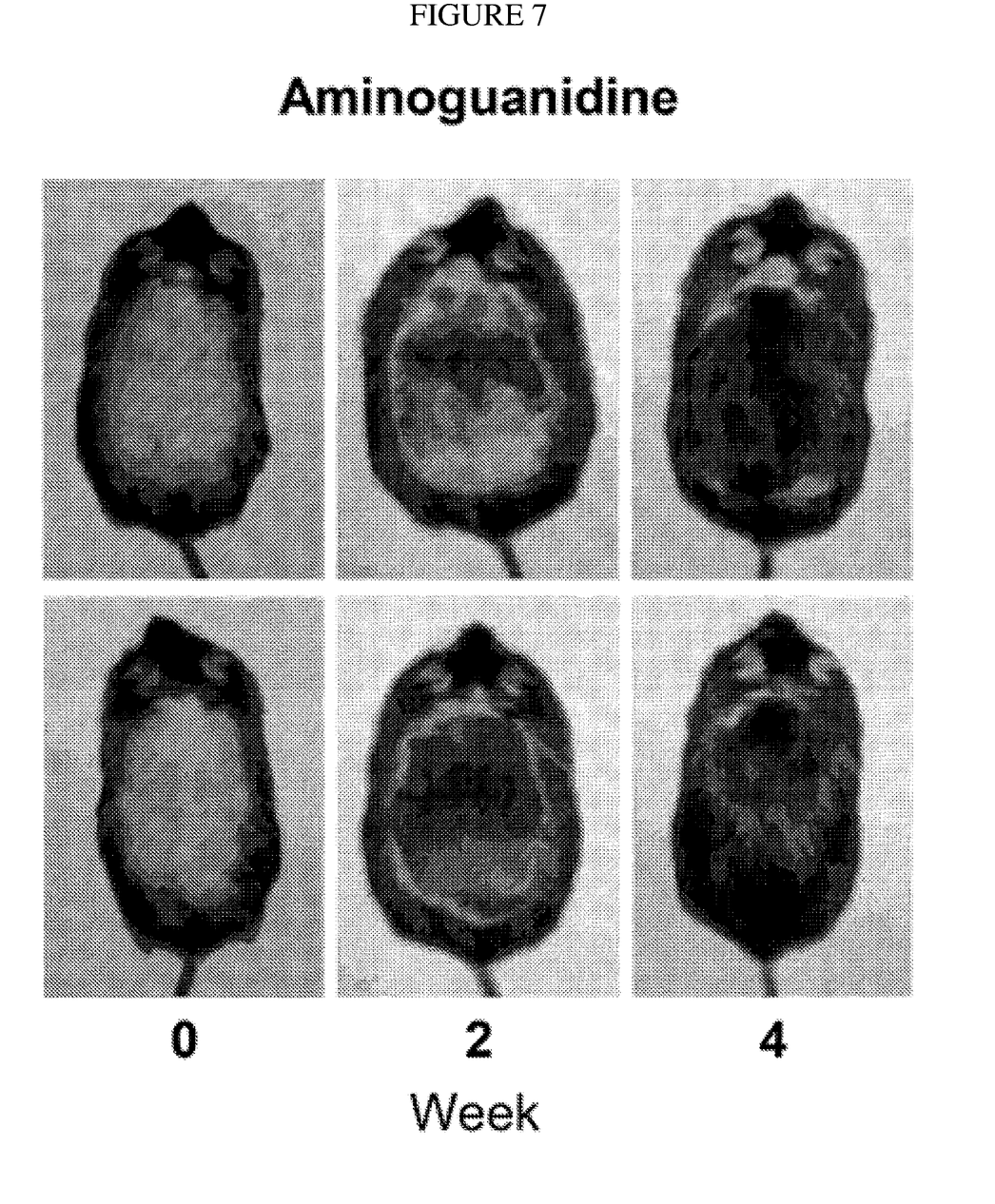
FIG. 7 A figure that shows the promotion (4 weeks) of hair growth by an iNOS inhibitor (aminoguanidine) (the upper row and lower row are different individuals).
Figure 8:
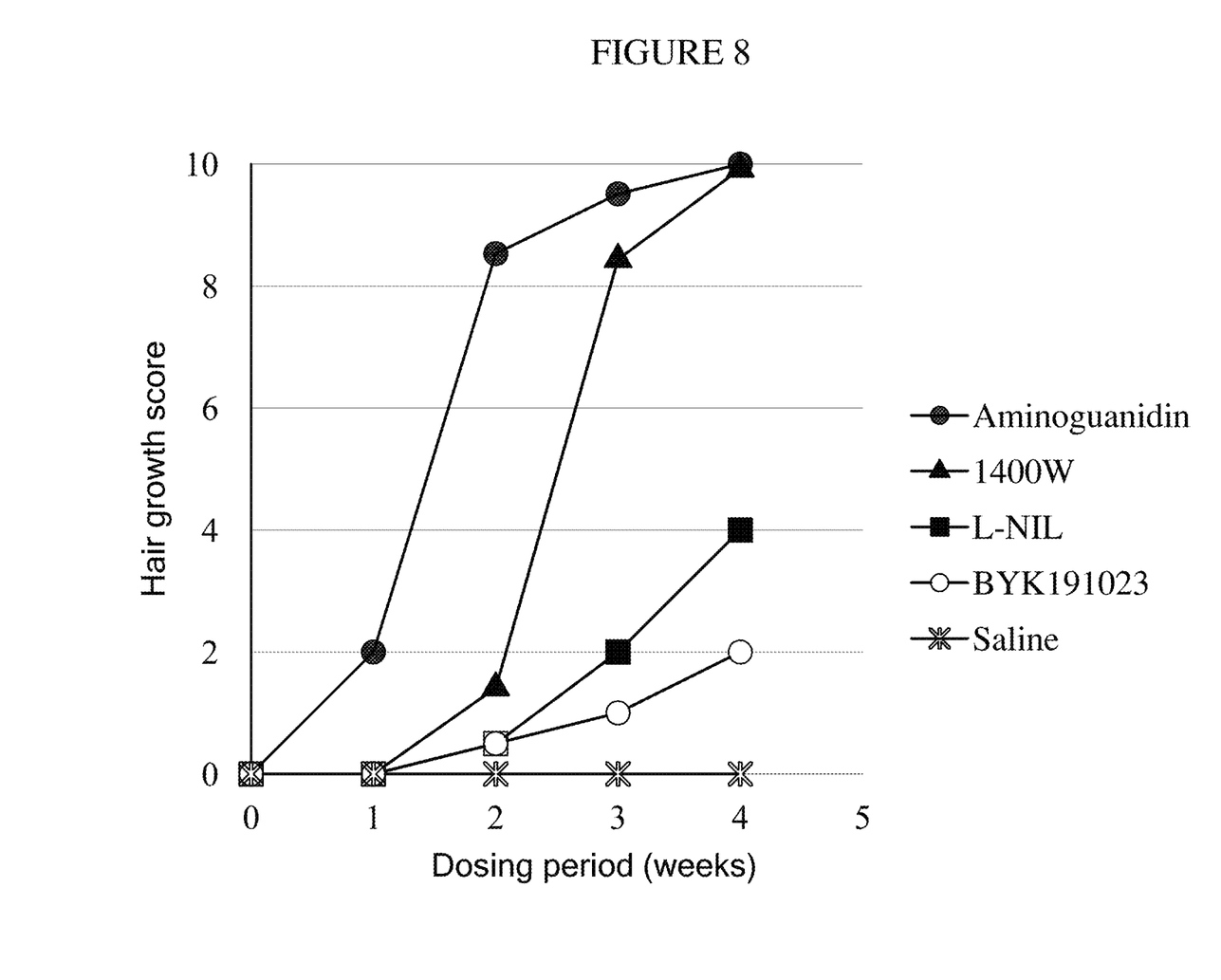
FIG. 8 A figure that shows the hair growth scores by iNOS inhibitors.

(Hair Growth Score Standard)
0=no hair growth
1=hair growth in less than 10% of the shaved area
2=hair growth in equal to or more than 10% and less than 20% of the shaved area 3=hair growth in equal to or more than 20% and less than 30% of the shaved area
4=hair growth in equal to or more than 30% and less than 40% of the shaved area
5=hair growth in equal to or more than 40% and less than 50% of the shaved area
6=hair growth in equal to or more than 50% and less than 60% of the shaved area
7=hair growth in equal to or more than 60% and less than 70% of the shaved area
8=hair growth in equal to or more than 70% and less than 80% of the shaved area
9=hair growth in equal to or more than 80% and less than 90% of the shaved area
10=hair growth in equal to or more than 90% of the shaved area As understood so far (for example, see WO2012/124614A1), hair growth was not seen in the control group in which only saline solution was administered to the ob/ob mouse (FIG. 3). Deposition of melanin pigments in the skin was observed two weeks after administration of 1400W, and widespread hair growth was confirmed in four weeks (FIG. 4). Compared to 1400W, L-NIL had a slightly slower timing of the deposition of melanin pigments, and the desposition was confirmed in three weeks from the start of the administration (FIG. 5). Similarly, deposition was confirmed in three weeks since the administration of BYK191023 began, and hair growth was identified in four weeks (FIG. 6). The area of hair growth was less with L-NIL and BYK191023 compared to 1400W. Deposition of melanin pigments in the skin was confirmed in one week from the start of the aminogunadine application, and hair growth was confirmed in two weeks. Widespread hair growth was confirmed in three weeks since the start of the application, and it returned to almost the same as the original condition in four weeks (FIG. 7). The hair growth scores of the administration group of each iNOS inhibitor and the control group are shown in FIG. 8.

As suggested by the observed results of the iNOS knockout mice, these data show that hair growth can be promoted by a number of arbitrary low-molecular iNOS inhibitors. That is, one may consider that hair growth can be regulated regardless of the means to inhibit iNOS. These results indicate that not only low-molecular iNOS inhibitors, other inhibitors such as antibodies, antisense oligonucleotides, siRNAs and such may also be used for the same purpose.

Example 3: Hair Growth Experiment Using Wild-Type Mice

In this experiment, the same method as Example 2 was used, except that the C3H mouse and C57BL/6 mouse were used. The whole back of the mouse was shaved using an electric shaver under anesthesia (mixed anesthesia of ketamine hydrochloride and xylazine hydrochloride) at 8 weeks of age, and the hair was removed with a commercially available depilatory cream (Epilat hair removal cream from Kracie Holdings, Ltd.). Application of aminoguanidine was carried out on the day the experiment began. The usage and dosage of the aminoguanidine used are as described below. Aminoguanidine was purchased from Tokyo Chemical Industry Co., Ltd. and dissolved to 10% (w/v) in saline solution, and 100 µl was applied to the epilation area. For the control group, saline solution was used. Consecutive application for five days from Monday to Friday was continued for three weeks, and the back was photographed daily.

Figure 9:
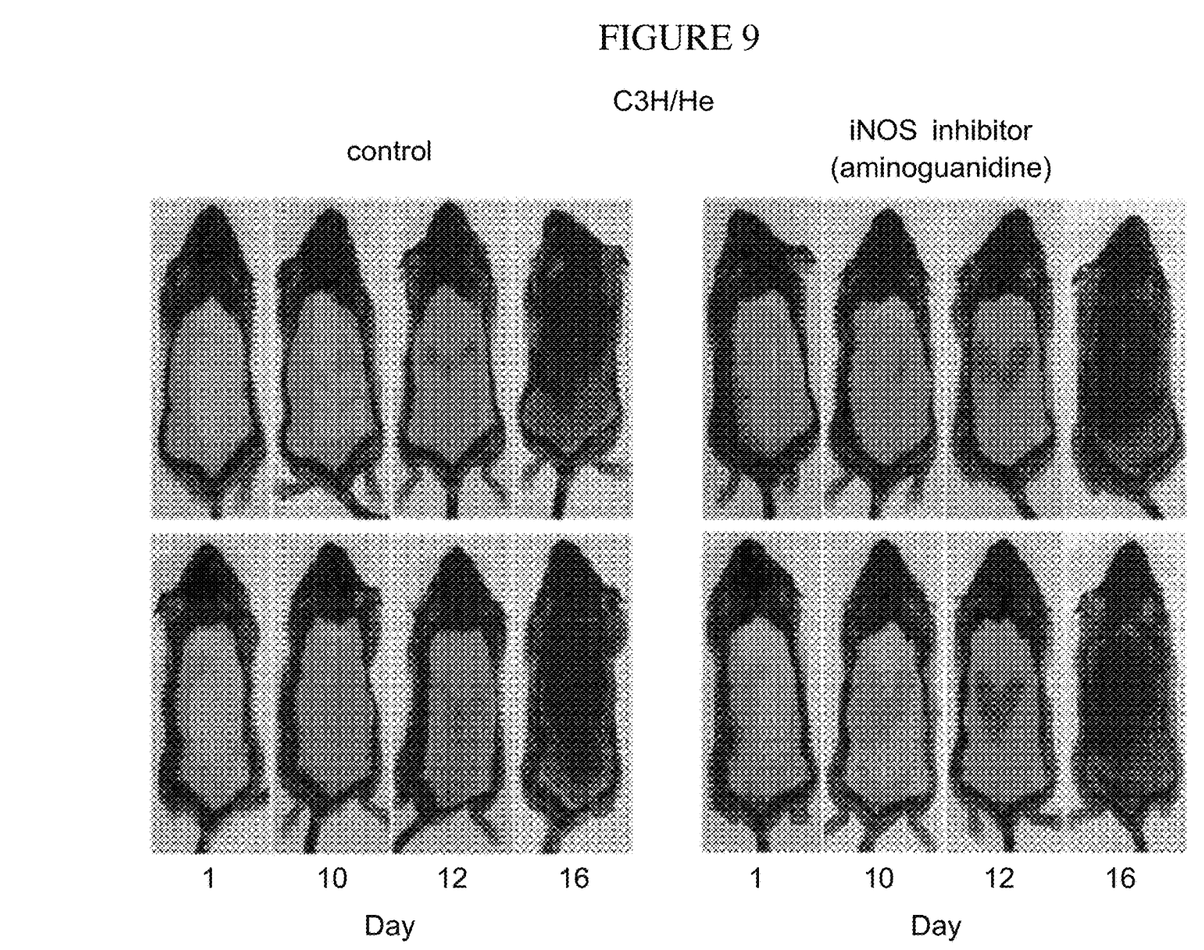
FIG. 9 A figure that shows the promotion (16 days) of hair growth by application of aminoguanidine in the C3H mice (two upper and lower rows on the right) (the upper row and lower row are different individuals). The two upper and lower rows on the left are the control mice.
Figure 10:
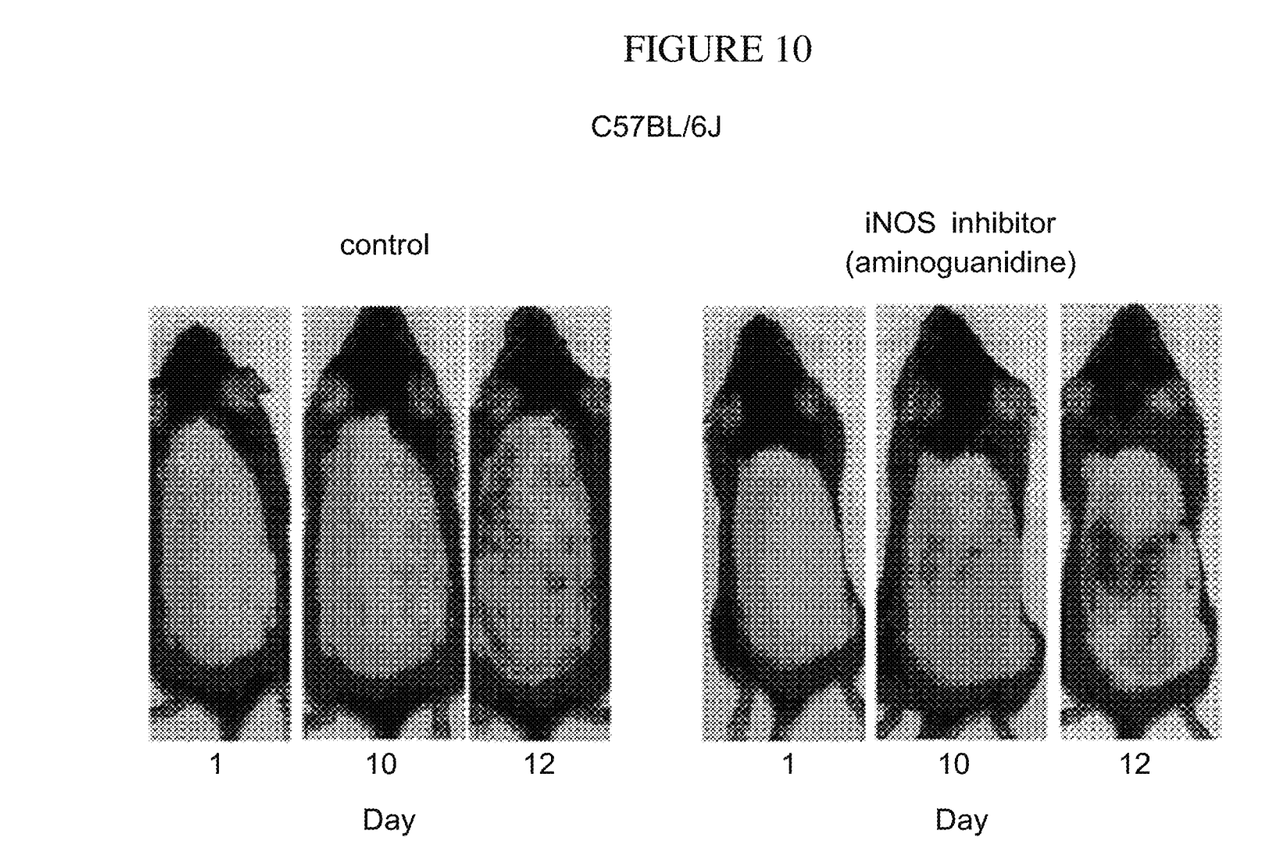
FIG. 10 A figure that shows the promotion (12 days) of hair growth by application of aminoguanidine (right) in the C57BL/6 mouse. The photos on the left are the control mouse.

As a result, shortening of the telogen phase by two to three days was seen in the aminoguanidine-applied group compared to the control group (FIGS. 9 and 10). Accordingly, it is demonstrated that promotion of hair growth by the iNOS inhibitor observed in the ob/ob mouse similarly occurred in normal wild-type mice as well.

Example 4: Analysis of the Gene Expression Levels in Skin Sections

In this experiment, the wild-type mouse and ob/ob mouse of 14 weeks of age were used. Skin sections were collected after hair removal of the back, and following RNA purification with an RNA purification kit (RNeasy Plus Universal Kit, Qiagen), cDNA was synthesized (High Capacity cDNA Reverse Transcription Kit, ABI) and the amount of RNA was quantified by a real-time PCR method. Thermal Cycler Dice® Real Time System from TaKaRa Bio was used for the thermal cycler, and TagMan® Gene Expression Assay (NOΩ: Mm_0040493_g1) from ABI was used for the TaqMan probe.

Figure 11:
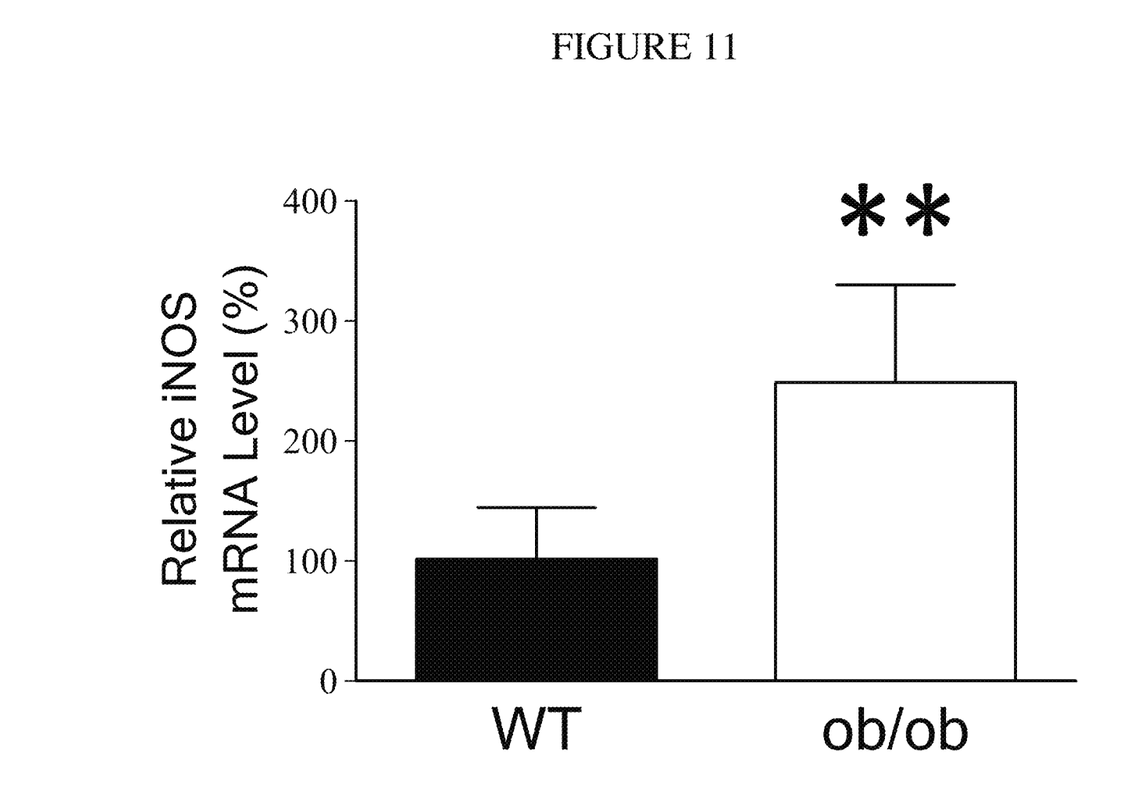
FIG. 11 A figure that shows the result of gene expression analysis in skin sections using a 14-week-old wild-type mouse and ob/ob mouse.

The results show that the iNOS gene was expressed in the ob/ob mouse at approximately 2.5 fold of that in the wild type (FIG. 11).

The present specification shows the preferred embodiments of the present invention, and it is clear to those skilled in the art that such embodiments are provided simply for the purpose of exemplification. A skilled artisan may be able to make various transformations, and add modifications and substitutions without deviating from the present invention. It should be understood that the various alternative embodiments of invention described in the present specification may be used when practicing the present invention. Further, the contents described in all publications referred to in the present specification, including patents and patent application documents, should be construed as being incorporated the same as the contents clearly written in the present specification by their citation.

INDUSTRIAL APPLICABILITY

As demonstrated in the Examples, the compositions of the present invention for use in the promotion of hair growth or hair restoration or prevention of hair loss have a remarkable hair growing effect, and the effect has been confirmed by iNOS inhibitors with different actions (inhibition by medicinal agents) and in knockout mice (genetic inhibition of iNOS). There is a high demand in the market for hair growing agents/hair tonics as there are few existing drugs or because their effects are not sufficient.

The invention claimed is:
1. A method of promoting hair growth or hair restoration or treating hair loss in a mammal in need thereof, comprising orally administering to the mammal or topically applying to the skin of the mammal a composition comprising an inducible Nitric Oxide Synthase (iNOS) inhibitor as an active ingredient and inhibiting iNOS in the mammal,
   wherein the iNOS inhibitor is aminoguanidine and
   wherein iNOS is inhibited to promote hair growth or hair restoration or to treat hair loss.
2. The method according to claim 1, wherein the composition is a pharmaceutical composition.
3. The method according to claim 1, wherein the composition is a cosmetic composition.
4. The method according to claim 1, wherein the composition is a beauty supplement.

5. The method according to claim 1, wherein the composition is an oral preparation.

6. The method according to claim 1, wherein the composition is topically applied to the skin of the mammal.

7. The method according to claim 1, wherein the mammal is a human.

8. The method according to claim 1, wherein the mammal is a dog, cat or sheep.

9. A method of promoting hair growth or hair restoration or treating hair loss in a mammal in need thereof, consisting of administering to the mammal a composition consisting of:
   an inducible Nitric Oxide Synthase (iNOS) inhibitor; and
   at least one selected from the group consisting of an excipient, an additive or a saline solution,
   wherein the iNOS inhibitor is
   wherein the composition is administered orally to the mammal, or topically applied to the skin of the mammal.

\* \* \* \* \*

UNITED STATES PATENT AND TRADEMARK OFFICE
CERTIFICATE OF CORRECTION

PATENT NO. : 11,931,325 B2
APPLICATION NO. : 15/769472
DATED : March 19, 2024
INVENTOR(S) : Shohei Shinozaki and Kentaro Shimokado It is certified that error appears in the above-identified patent and that said Letters Patent is hereby corrected as shown below:

In the Specification

In Column 4, Line 18, delete "exisiting" and insert --existing--.

In Column 4, Line 33, delete "NOΩ)" and insert --NOS2)--.

In Column 4, Line 35, delete "(NO53)." and insert --(NOS3).--.

In Column 4, Line 36, delete "Nitrix" and insert --Nitric--.

In Column 4, Line 66, delete "Aminoguandine" and insert --Aminoguanidine--.

In Column 7, Line 61, delete "1;" and insert --1:--.

In Column 9, Line 25, delete "desposition" and insert --deposition--.

In Column 9, Line 33, delete "aminogunadine" and insert --aminoguanidine--.

In Column 10, Line 19, delete "TagMan®" and insert --TaqMan®--.

In Column 10, Line 20, delete "(NOΩ:" and insert --(NOS2:--.

In the Claims

In Column 11, Claim 9, Line 15, after "is" insert --aminoguanidine--.

Signed and Sealed this
Eleventh Day of June, 2024

Katherine Kelly Vidal
*Director of the United States Patent and Trademark Office*